United States Patent
Ball et al.

(10) Patent No.: US 8,658,820 B2
(45) Date of Patent: Feb. 25, 2014

(54) CATALYST SYSTEMS FOR THE PRODUCTION OF ACIDS

(75) Inventors: George A. Ball, Hampstead, NC (US); Joseph C. Gentry, Houston, TX (US); Joseph P. Weller, Angleton, TX (US); Zhongyi Ding, Katy, TX (US); John R. H. Wilson, Essex (GB); Meritxell Guino, York (GB); Weihua Jin, Katy, TX (US)

(73) Assignee: GTC Technology US, LLC, Houston, TX (US)

( * ) Notice: Subject to any disclaimer, the term of this patent is extended or adjusted under 35 U.S.C. 154(b) by 459 days.

(21) Appl. No.: 12/993,806

(22) PCT Filed: May 26, 2009

(86) PCT No.: PCT/US2009/045199
§ 371 (c)(1),
(2), (4) Date: Jan. 21, 2011

(87) PCT Pub. No.: WO2009/143531
PCT Pub. Date: Nov. 26, 2009

(65) Prior Publication Data
US 2011/0108763 A1 May 12, 2011

Related U.S. Application Data

(60) Provisional application No. 61/055,890, filed on May 23, 2008.

(51) Int. Cl.
*C07C 51/21* (2006.01)
*C07C 63/26* (2006.01)
(52) U.S. Cl.
USPC .......................................... 562/414; 562/412
(58) Field of Classification Search
None
See application file for complete search history.

(56) References Cited

U.S. PATENT DOCUMENTS

| 5,068,406 A | 11/1991 | Holzhauer et al. |
| 6,359,186 B1 | 3/2002 | Hotier et al. |
| 7,314,954 B1 * | 1/2008 | Yen .............................. 562/414 |
| 2005/0272951 A1 | 12/2005 | Noe' |

FOREIGN PATENT DOCUMENTS

| EP | 0335501 A1 | 10/1989 |
| JP | 08-157415 | 6/1996 |
| JP | 14-543172 | 12/2002 |
| KR | 10-1999-0031350 | 5/1999 |

OTHER PUBLICATIONS

International Search Report; mailed Jan. 14, 2010; Korean Intellectual Property Office—Authorized Officer: Kim Rahn.

* cited by examiner

*Primary Examiner* — Yevegeny Valenrod
(74) *Attorney, Agent, or Firm* — Winstead PC (57) ABSTRACT

Various embodiments of the invention herein described generally relate to novel processes for the production of aromatic acids by fixed bed catalytic oxidation of aromatic compounds carrying at least one oxidizable substituent group attached directly to the carbon atom of the corresponding aromatic nucleus. In an embodiment, a novel oxidation process of the present invention comprises the steps of: a) catalytically oxidizing, with an oxidation catalyst, a liquid phase aromatic acid precursor in the presence of a gaseous oxygen source; b) separating a finished product; c) purging the solvent and the oxidation catalyst; d) optionally recycling at least a portion of the solvent into the oxidation reactor; e) recovering at least a portion of the oxidation catalyst; f) recharging the at least a portion of the oxidation catalyst over a solid recharging catalyst bed; and (g) feeding a reactivated oxidation catalyst to the oxidation reactor.

6 Claims, 7 Drawing Sheets

Scheme 1

Figure 7

Scheme 2

Figure 8

Scheme 3

Figure 9

Scheme 4

Figure 10

Scheme 5

Figure 11

Scheme 6

CATALYST SYSTEMS FOR THE PRODUCTION OF ACIDS

BACKGROUND OF THE INVENTION

Background

Meta-xylene and Para-xylene are valuable chemical intermediates used in the production of isophthalic acid and terephthalic acid (IPA/fA (or CIPA/CTA)), purified or crude, used in the production of resins and various other items. An oxidation step is a common process step in the production of IPA/TA or CIPA/CTA. As is well known, processes for the production of monocarboxylic and polycarboxylic aromatic acids are normally carried out in liquid phase in either continuous or discontinuous processes, and using as substrates aromatic compounds carrying at least one oxidizable substituent group attached directly to the carbon atom of the corresponding aromatic nucleus.

SUMMARY OF THE INVENTION

In general, various embodiments of the present invention comprise systems and processes for oxidizing a precursor comprising the steps of:
 a) catalytically oxidizing a precursor in the presence of an oxygen source, and
 b) recharging said at least a portion of said oxidation catalyst over a solid recharging catalyst bed.

Various embodiments comprise systems and processes for producing an acid, said process comprising the steps of:
 a) catalytically oxidizing, with an oxidation catalyst, a liquid phase aromatic acid precursor in the presence of a gaseous oxygen source;
 b) separating a finished product;
 c) purging said solvent and said oxidation catalyst;
 d) recovering at least a portion of said oxidation catalyst;
 e) recharging said at least a portion of said oxidation catalyst over a solid recharging catalyst bed; and,
 f) feeding a reactivated oxidation catalyst to said oxidation reactor.
In various embodiments, steps (a) to (f) are performed in a continuous cycle or repeated at least one time.

In a particular embodiment, a recharging catalyst system is used in a process for converting a feed stream comprising at least meta-xylene, para-xylene, and ethylbenzene into at least one product stream comprising isophthalic acid and terephthalic acid (IPA/TA), said process comprising the steps of:
 a. removing ethylbenzene from said feed stream to produce an ethylbenzene depleted feed stream;
 b. removing ortho-xylene from said ethylbenzene depleted feed stream to produce an ortho-xylene depleted feed stream;
 c. oxidizing said ethylbenzene depleted and said ortho-xylene depleted feed stream to produce a product stream, said product stream comprising IPA/TA in a proportion between 0.5% and about 99.5% IPA and about 0.5% and about 99.5% TA; and,
 d. recharging said at least a portion of said oxidation catalyst over a solid recharging catalyst bed.

Various further embodiments disclose a system for the production of a product stream comprising isophthalic acid and terephthalic acid (IPA/TA) from a feed stream comprising at least meta-xylene and para-xylene, said system comprising:
 a. an ortho-xylene removal zone;
 b. a co-oxidation zone;
 c. a solid bed catalyst, said solid bed catalyst capable of regenerating said oxidation catalyst;
wherein said ortho-xylene removal zone is capable of removing components heavier than meta-xylene and components heavier than para-xylene, and wherein said ortho-xylene removal zone is capable of producing an ortho-xylene depleted stream, and wherein said co-oxidation zone is capable of oxidizing both meta-xylene and para-xylene into crude isophthalic acid and crude terephthalic acid (C-IPA/C-TA).

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE INVENTION

The following definitions and explanations are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, $3^{rd}$ Edition. Definitions and/or interpretations should not be incorporated from other patent applications, patents, or publications, related or not, unless specifically stated in this specification or if the incorporation is necessary for maintaining validity.

As used herein, the term "acetic acid", also known as ethanoic acid, means and refers to an organic chemical compound, giving vinegar its sour taste and pungent smell. Its structural formula is represented as $CH_3COOH$. Pure, water-free acetic acid (glacial acetic acid) is a colorless liquid that attracts water from the environment (hygroscopy), and freezes below 16.7° C. (62° F.) to a colorless crystalline solid. It is a weak acid because at standard temperature and pressure the dissociated acid exists in equilibrium with the undissociated form in aqueous solutions, in contrast to strong acids, which are fully dissociated. Acetic acid is a structurally simple carboxylic acids. It is a chemical reagent and industrial chemical that is used in the production of polyethylene terephthalate mainly used in soft drink bottles; cellulose acetate, mainly for photographic film; and polyvinyl acetate for wood glue, as well as synthetic fibres and fabrics. In households diluted acetic acid is often used in descaling agents. In the food industry acetic acid is used under the food additive code E260 as an acidity regulator.

As used herein, the term "aromatic" means and refers to aromaticity, a chemical property in which a conjugated ring of unsaturated bonds, lone pairs, or empty orbitals exhibit a stabilization stronger than would be expected by the stabilization of conjugation alone. It can also be considered a manifestation of cyclic delocalization and of resonance. This is usually considered to be because electrons are free to cycle around circular arrangements of atoms, which are alternately single- and double-bonded to one another.

As used herein, the term "aliphatic" means and refers to compounds comprising carbon atoms that are capable of being joined together in straight chains, branched chains, or rings (in which case they are called alicyclic). They can be joined by single bonds (alkanes), double bonds (alkenes), or triple bonds (alkynes). A simple aliphatic compound is methane ($CH_4$). Aliphatics include alkanes such as fatty acids and paraffin hydrocarbons, alkenes (such as ethylene) and alkynes (such as acetylene).

As used herein, a "fluid" is a continuous, amorphous substance whose molecules move freely past one another and that has the tendency to assume the shape of its container, for example, a liquid or a gas.

As used herein, the term "mixed xylene" or "mixed xylenes" means and refers to an aromatic stream of hydrocarbons comprising about 20 to about 80 wt % meta-xylene, about 10 to about 60 wt % para-xylene, optionally about 10 to about 60 wt % ortho-xylene, and optionally about 0.1 to about 30 wt % ethylbenzene.

As used herein, the term "oxidizable substituent group" means and refers to any substituent in which a carbon atom is bonded directly to the aromatic nucleus and which, as a result of oxidation, is converted into a carboxyl group.

Other than in the operating examples, or where otherwise indicated, all numbers expressing quantities of components used herein are to be understood as modified in all instances by the term "about".

An improved process has now surprisingly been found for the oxidation of an aromatic or aliphatic compound with a supported rechargeable catalyst system, the compound containing at least one oxidizable substituent group directly attached to the carbon atom of the corresponding aromatic ring in which the aromatic compound is reacted with molecular oxygen and/or air. In various embodiments, the compound is aliphatic. In various other embodiments, the compound is aromatic. In various embodiments, the improved process is performed at an absolute pressure lower than 10 bar and at a temperature of about 50° C. to about 250° C.

Accordingly, in general, various embodiments of the present invention comprise a novel oxidation process. More particularly, various embodiments of the present invention generally comprise the steps of a) catalytically oxidizing, with an oxidation catalyst, a liquid phase aromatic precursor in the presence of a gaseous oxygen source; b) separating a finished product; c) purging the solvent and the oxidation catalyst; d) optionally recycling at least a portion of the solvent into the oxidation reactor; e) recovering at least a portion of the oxidation catalyst; f) recharging the at least a portion of the oxidation catalyst over a solid recharging catalyst bed; and feeding a reactivated oxidation catalyst to the oxidation reactor. In various embodiments, steps (a) to (e) are capable of being carried out in a closed and continuous cycle.

Exemplary, non-limiting embodiments and/or disclosures of oxidation catalysts are disclosed in U.S. Pat. Nos. 6,355,835; 6,160,170; 6,670,502; 6,521,786; 6,761,860; 6,565,754; and, 6,833,472, the contents of which are hereby incorporated by reference, as if they were presented herein in their entirety.

Process conditions of the present invention are capable of varying significantly. In various embodiment, a novel process or system of the present invention is performed at a temperature of from about 50.0° C. to about 250° C. In an alternate embodiment, a novel process or system of the present invention is performed at a temperature of from about 75.0° C. to about 200° C. In an alternate embodiment, a novel process or system of the present invention is performed at a temperature of from about 100° C. to about 150° C.

The oxidizing agent is generally gaseous molecular oxygen, preferably diluted with an inert gas; for obvious reasons of practicality, air (optionally enriched with molecular oxygen) is the gaseous mixture most commonly used for this purpose. The oxidation reaction is normally carried out using as solvent an aqueous organic acid, preferably acetic acid, normally with a water content of from 2 to 15%.

In various embodiment, a novel process or system of the present invention is performed at a pressure of from about 0.5 bar to about 10 bar. In an alternate embodiment, a novel process or system of the present invention is performed at a pressure of from about 1 bar to about 8 bar. In an alternate embodiment, a novel process or system of the present invention is performed at a pressure of from about 2 bar to about 5 bar.

An oxidation reaction solvent of various embodiments of the present invention normally comprises C1-C6 aliphatic acids or mixtures thereof. In an embodiment, a solvent is at least partially acetic acid. In an alternate embodiment, the oxidation solvent is at least partially formic acid. Generally any aliphatic acid will work in embodiments of the present invention. Typical concentrations of acids in the oxidation solvent The oxidizable aromatic precursors are normally selected from the group consisting of toluene, p-xylene, m-xylene, mesitylene and 2,6-dimethyl-naphtalene Generally, however, any aromatic compound/precursor can be chosen.

Various oxidation catalysts are capable of use with embodiments of the present invention. In various embodiments, a catalytic complex generally comprises one or more metals, normally in the form of salts soluble in the reaction solvent. Typically, a suitable activator is used to enhance the catalyzed oxidation reaction. The metal will undergo a reduction in its oxidation number during catalysis and a solid bed catalyst as herein described will be used to increase the valence number and retain the metal's catalytic effect.

The addition of activators to increase the valence is avoided because anything added to the reaction must be removed from the reaction.

Various embodiments of a catalyst of the present invention are normally selected from metals belonging to groups VIII, VIIB and IVB. Suitable metals for various embodiments include, but are not limited to, scandium, yttrium, lanthanum, neodymium, gadolinium, thorium, zirconium or hafnium, cobalt., platinum, palladium and/or ruthenium.

Suitable activators include acetyls, aldehydes, ketones, bromine, zirconium acetate, and/or the like.

A solid catalyst bed is used to regenerate spent catalyst, or catalyst that has been reduced in valence. In various embodiments, the solid catalyst bed is supported on a silica substrate or other suitable substrate.

Therefore, various embodiments of the present invention generally provide systems and/or processes for regenerating an oxidation catalyst. Various embodiments of the present invention can be used with a variety of petrochemical processes. An embodiment of the present invention can be used with systems and/or processes for producing acids, such as an oxidation catalyst for a process for producing a product stream comprising isophthalic acid and/or terephthalic acid (IPA/TA).

In general, the feed stream for a process for producing a product stream comprising IPA/TA with an oxidation catalyst process or system as herein disclosed comprises from about 1 wt % to about 40 wt % ethylbenzene, from about 20 wt % to about 80 wt % meta-xylene, from about 5 wt % to about 30 wt % ortho-xylene, and from about 0.5 wt % to about 40 wt % para-xylene. In an alternate, the hydrocarbon feed stream comprises from about 1 wt % to about 20 wt % ethylbenzene, from about 50 wt % to about 65 wt % meta-xylene, from about 20 wt % to about 30 wt % ortho-xylene, and from about 0 5 wt % to about 5 wt % para-xylene. In an alternate, the hydrocarbon feed stream comprises from about 0.1 wt % to about 50 wt % ethylbenzene, from about 0.1 wt % to about 99.9 wt % meta-xylene, from about 0.1 wt % to about 99.9 wt % ortho-xylene, and from about 0.1 wt % to about 99.9 wt % para-xylene. In alternate embodiment, the feed stream comprises a mixed xylene feed stream comprising about 20% ethyl benzene, about 20% ortho-xylene, about 40% meta-xylene, and about 20% para-xylene.

Figure 1:
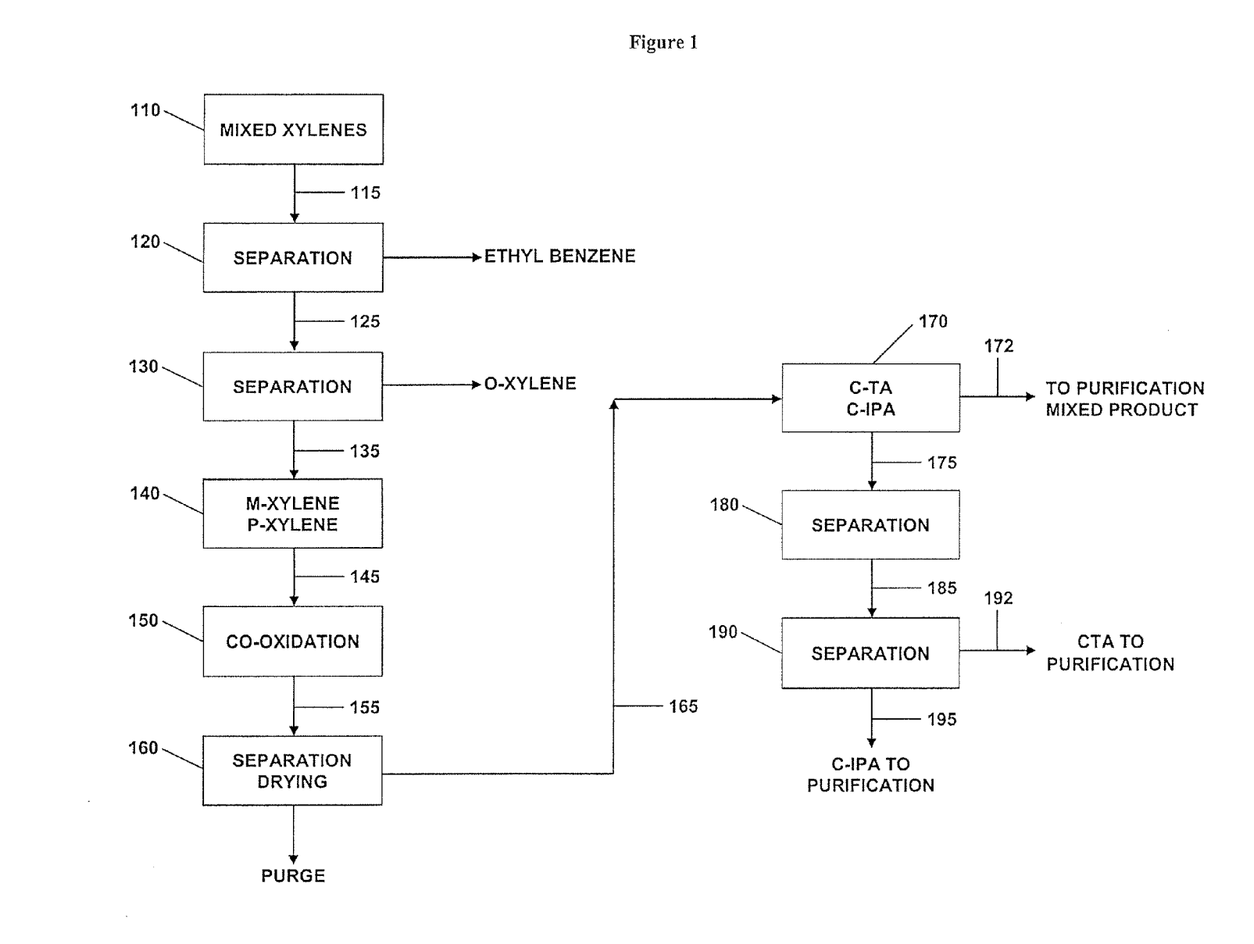
FIG. 1 is an illustration of a flow diagram showing an embodiment of a process of the present invention.

Referring now to FIG. 1, an embodiment of a base flow diagram depicting generalized process steps is disclosed. In general, various embodiments of the present invention comprise the steps of catalytically oxidizing in an oxidation reactor 20, in the presence of a solvent and an oxidation catalyst comprising at least partially reactivated catalyst, a liquid phase aromatic precursor in the presence of a gaseous oxygen source;

withdrawing 25 an oxidate from the oxidation reactor 20;

separating 30 a finished product from the oxidate wherein a finished product depleted oxidate is produced;

withdrawing 35 the a finished product depleted oxidate;

optionally recycling 37 at least a portion of the solvent into the oxidation reactor 20;

recovering 40 at least a portion of the oxidation catalyst from the finished product depleted oxidate stream, and optionally solvent depleted stream, 39;

recycling 45 the recovered catalyst;

reactivating 10 the at least a portion of the oxidation catalyst over a solid recharging catalyst bed 10; and, feeding 7 a reactivated oxidation catalyst to the oxidation reactor 20.

Optionally, additional catalyst can be added to make-up for any lost and/or corrupted catalyst, It is expected that some amount of catalyst will be lost during catalyst recovery.

Various other operational arrangements exist and would be understood by one of ordinary skill in the art, such as, but not limited to, recycling solvent from the catalysts recovery unit, or, providing storage for the spent catalyst and/or providing storage for the reactivated catalyst, and/or the like.

Generally, any solvent will work with various embodiments of the present invention, as would be appreciated by one of ordinary skill in the art. A non-exclusive list of solvents for use in oxidation include acetic acid, water, other acids, and/or the like. Likewise, generally, all catalysts useful for oxidation are capable of use with various embodiments of the present invention. A non-exclusive list of catalysts include Cobalt, Manganese, Bromine, Fluorine, and/or the like.

After an oxidation process, the resulting stream will contain catalyst and solvent that should be removed, such as by a filter and a dryer. The catalyst is separated from the resulting stream and can be recycled and recharged or discarded. The solvent collected can be recycled or passed off as waste. Various dryers and/or filters are capable of performing the separating and/or drying. At this point, the resulting stream comprises a crude, or not purified, product stream comprising C-TA and C-IPA.

Accordingly, disclosed herein are various processes for producing an acid utilizing a recharging catalyst bed of the present invention, said process comprising the steps of:

a) catalytically oxidizing, with an oxidation catalyst, a liquid phase aromatic acid precursor in the presence of a gaseous oxygen source;

b) separating a finished product;

c) purging said solvent and said oxidation catalyst;

d) recovering at least a portion of said oxidation catalyst;

e) recharging said at least a portion of said oxidation catalyst over a solid recharging catalyst bed; and, f) feeding a reactivated oxidation catalyst to said oxidation reactor.

Further disclosed herein are processes for converting a feed stream comprising at least meta-xylene, para-xylene, and ethylbenzene into at least one product stream comprising isophthalic acid and terephthalic acid (IPA/TA), said process comprising the steps of:

a) removing ethylbenzene from said feed stream to produce an ethylbenzene depleted feed stream;

b) removing ortho-xylene from said ethylbenzene depleted feed stream to produce an ortho-xylene depleted feed stream;

c) oxidizing said ethylbenzene depleted and said ortho-xylene depleted feed stream to produce a product stream, said product stream comprising IPA/TA in a proportion between 0.5% and about 99.5% IPA and about 0.5% and about 99.5% TA; and, d) recharging said at least a portion of said oxidation catalyst over a solid recharging catalyst bed.

In various embodiments, an acid mixture produced according to the process described herein.

Also disclosed herein are systems utilizing a recharging catalyst bed of the present invention for the production of a product stream comprising isophthalic acid and terephthalic acid (IPA/TA) from a feed stream comprising at least meta-xylene and para-xylene, said system comprising:

a. an ortho-xylene removal zone;

b. a co-oxidation zone;

c. a solid bed catalyst, said solid bed catalyst capable of regenerating said oxidation catalyst;

wherein said ortho-xylene removal zone is capable of removing components heavier than meta-xylene and components heavier than para-xylene, and wherein said ortho-xylene removal zone is capable of producing an ortho-xylene depleted stream, and wherein said co-oxidation zone is capable of oxidizing both meta-xylene and para-xylene into crude isophthalic acid and crude terephthalic acid (C-IPA/C-TA).

The invention may be embodied in other specific forms without departing from its spirit or essential characteristics.

The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

Feedstock

In general, any aromatic $C_8$ mixture containing ethylbenzene and a xylene may be used as feed to the process of this invention. In general, the feed stream comprises from about 1 wt % to about 25 wt % ethylbenzene, from about 20 wt % to about 80 wt % meta-xylene, from about 5 wt % to about 30 wt % ortho-xylene, and from about 0.5 wt % to about 20 wt % para-xylene. In an alternate, the hydrocarbon feed stream comprises from about 1 wt % to about 20 wt % ethylbenzene, from about 50 wt % to about 65 wt % meta-xylene, from about 20 wt % to about 30 wt % ortho-xylene, and from about 0 5 wt % to about 5 wt % para-xylene. In alternate embodiment, the feed stream comprises a mixed xylene feed stream comprising about 20% ethyl benzene, about 20% ortho-xylene, about 40% meta-xylene, and about 20% para-xylene.

Process Conditions

In accordance with the present invention, the above described feedstock may be contacted with the catalyst system under suitable conversion conditions to effect oxidation. Examples of these conversion conditions include a temperature of from about 100° C. to about 200° C., a pressure of from 0 psig to about 300 psig, An alternative to these conversion conditions may include a temperature of from about 150° C. to about 175° C., a pressure of from about 50 psig to about 100 psig.

Various embodiments of the present invention are capable of use in the production of acids, which acids are then capable of being converted into a polymer, such as a polyester polymer. Polyester polymers are used in the production of various items, including, but not limited to a bottle, a film, a fiber, or an injection molded article.

In yet a further embodiment, a recharging catalyst system of the present invention can be used with a process for converting a feed stream comprising at least meta-xylene and para-xylene into at least one product stream comprising isophthalic acid and terephthalic acid (IPA/TA) is disclosed, the process comprising the steps of:

EXAMPLES

Figure 2:
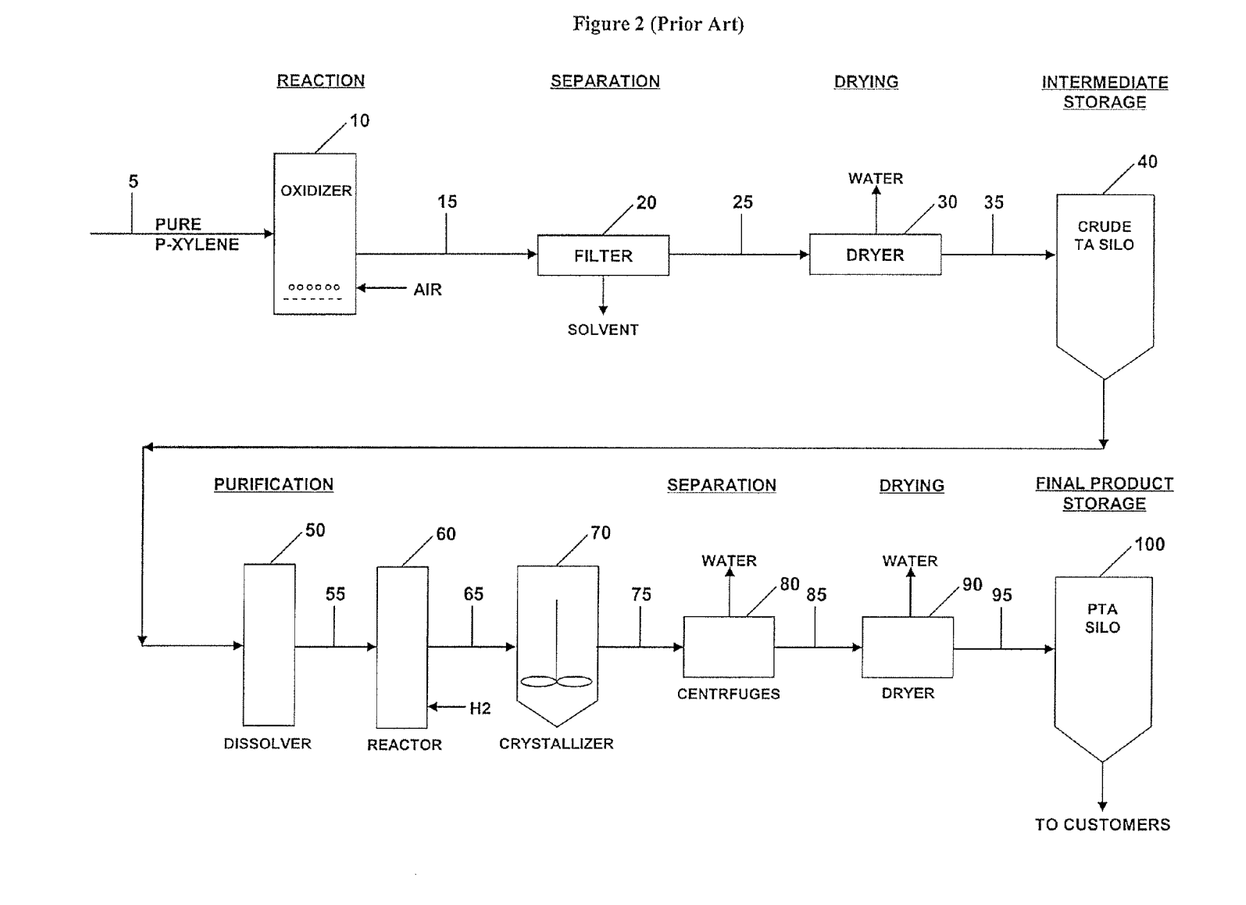
FIG. 2 is an illustration of the oxidation reaction of para-xylene to terephthalic acid wherein many intermediates of the reaction are illustrated.

Using para-xylene to as an example, the oxidation reaction goes through a number of steps as illustrated in FIG. 2. In order to compose the effectiveness of Co3+ TO Co2+ in the oxidation of xylenes, it was decided to focus on the early phase of the oxidation. HPLC is an ideal analytical method for monitoring the early phase oxidation. Reaction progress was measured by looking at the disappearance of the starting para-xylene and meta-xylene (traces at a retention time of 3.2 minutes) and the appearance and disappearance of new peaks in the HPLC traces as the reaction proceeds. The intermediate oxidation products as illustrated occur at 2.6, 2.4 and 1.9 minutes. It is known that TA occur in the HPLC traces (1.9 and 1.5 minutes).

Method to Convert Co(II) Acetate to Co(III) Acetate a) Oxidation of Co Using Peracetic Acid A solution comprising Co(III) was prepared according to the procedure as follows: Cobalt (II) acetate tetrahydrate (1 equivalent) was dissolved in acetic acid to give a pink solution. A solution of peracetic acid (40% in acetic acid/water, 1 equivalent) was added dropwise while stirring the mixture. The resulting exothermic reaction produces the Cobalt (III) as is evidenced by the color of the solution changing to green. This solution can be stored at room temperature without decomposition. Alternatively, the solvent can be evaporated and the green solid is stable when stored at room temperature. No noticeable changes of the Co(III) acetate catalyst have been observed on standing 6 weeks.

The formation of the Co(III) acetate solution is proved by a color change and also by HPLC. The traces of the Co solution at 0.369 minutes disappeared completely to give a new peak at 0.262 minutes of the Co solution.

HPLC: Agilent Technologies 1100 Series. Phenomenex C18 column (50×4.60 mm, 3 mm). Method: 90% H (0.1% formic acid)—10% acetonitrile (0.1% formic acid) to 10% H (0.1% formic acid)—90% acetonitrile (0.1% formic acid). Flow: 2.6 mL/min. Time: 5 minutes. Injection volume: 20 pL. UV detector at 254 nm.

It is envisaged that a number of other oxidants would also work in place of peracetic acid. Generally, any oxidant is capable of being used. In an embodiment, the oxidant is heterogeneous catalyst with a peroxo functional group. As used herein, "peroxo" or "peroxy" indicates replacement of an oxygen atom by the —O—O— group in the suffix.

Oxidation of Xylenes Using CO(II) Acetate and CO(III) Acetate

The reported reaction procedure disclosed in U.S. Pat. No. 6,670,502 was used for purposes of oxidizing the xylenes, the contents of which is hereby incorporated by reference in its entirety. It was discovered that there should be a sufficient concentration of Cobalt (III) present to rapidly start the oxidation of the xylene.

An oxidation reaction of a meta and para xylene mixture using a Cobalt (II) acetate and Zirconium acetate catalyst system in acetic acid was investigated, with the concentration of Co in the reaction mixture based on the total charge to the reactor corresponding to approximately 7000 ppm. The reaction mixture was heated at 100° C. and it was found that there was a long induction period (>6 hours) until the mixture of xylenes started to convert into other reaction intermediates (2.6 and 2.4 minutes). It was observed that the reaction only begun when the color of the reaction mixture changed from pink/purple to a brownish green. The starting xylenes (HPLC traces at 3.2 minutes) were consumed after long reaction times but the reaction did not go to completion.

Oxidation occurred when using acetaldehyde as the promoter with Cobalt (II) acetate. A concentration of about 3750 ppm of Co was used and the reaction mixture was heated at 50-60° C. An induction period of approximately 15 minutes was needed in order to observe a change of color from pink to green solution. After 3 hours, a conversion of 80% into the intermediate at a retention time of 2.6 minutes in the HPLC traces was found. However, much longer reaction times were required in order to get a full conversion into the intermediate at a retention time of 2.3 minutes and TA was not obtained after up to 48 hours.

With a catalyst system comprising Cobalt (II) acetate, Manganese acetate and potassium bromide a longer induction time of 5 hours and incomplete oxidation was observed.

Experiments conducted at 120° C. using just Cobalt (III) acetate without any promoters in air and using acetic acid as solvent resulted in much quicker oxidation than Cobalt (II) acetate with the promoters as described above, leading to rapid consumption of xylenes, as indicated by the green solution turning pink-purple after approximately an hour. Under identical reaction conditions using Co(II) there was a long induction period before any early phase oxidation.

Figure 5:
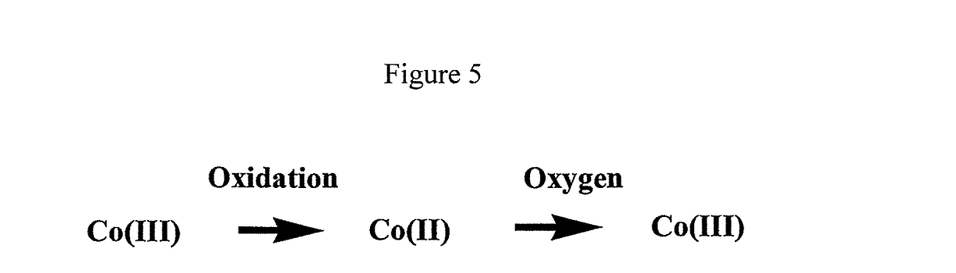
FIG. 5 is an illustration of illustrates a Cobalt (III) reaction pattern.

After the oxidation of the xylenes, in order to be able to reuse Cobalt (III) catalysts system, it was found necessary that the reaction conditions and reagents have to be sufficient in order to re-oxidize the Cobalt (II) back to Cobalt (III). FIG. 5 illustrates a Cobalt (III) reaction pattern. Several literature procedures have been followed to attempt the oxidation reaction of para and meta xylene to terephthalic acid.

Using para xylene as an example, the oxidation reaction goes through a number of steps as illustrated in FIG. 2.

Oxidation of Xylenes to Terephthalic Acid

Using para xylene as an example, the oxidation reaction goes through a number of steps as illustrated in FIG. 2.

Varying Concentrations of Co (III) Acetate and Reaction

A study involving different amounts of Co(III) acetate present in the mixture in order to carry out the oxidation reaction was performed. The reaction was followed by HPLC every hour up to 7 hours. Four different concentrations of Co were investigated: 16000 ppm, 11000 ppm, 6000 ppm and 1800 ppm. The bigger the amount of Co (16000 and 11000 ppm), the fastest conversion obtained (see light blue and brown curves with about 70-80% conversion after 1 hour reaction). However, it was observed that the conversion remained constant for the next 6 hours, while the color of the mixture changed from green to dark purple and finally pink. In both cases, the major compound formed corresponded to intermediate 1 with less than 10% of intermediate 2. On the other hand, with the least amount of Co present in the mixture (6000 and 1800 ppm), the oxidation reaction was slower at the beginning but it increased conversions with longer reaction times (orange and dark blue curves, from about 50% conversion to about 80-90% conversion). Both reaction mixtures remained green for a few hours and afterwards changed to dark brown/purple (6000 ppm) and dark blue/brown (1800 ppm). When utilizing 6000 ppm of Co(III) acetate, the xylenes were converted faster into intermediate 2 and 3, whereas with the solution of 1800 ppm, xylenes were again mainly converted into intermediate 1.

Preparation of Heterogeneous Catalysts

It was determined that peracetic acid is a suitable oxidant in order to synthesize a green Co(III) acetate solution. Thus, a variety of heterogeneous catalysts with a "peroxo" functionality should be capable of oxidizing a solution of Co(II) acetate to Co(III) acetate by mimicking the peracetic acid.

The preparation of a silica-supported peroxycarboxylic acid is known in then art. In general, a carboxylic acid silica can be treated with methanesulfonic acid and hydrogen peroxide to form the —COOH silica which is capable of use for the epoxidation of alkenes. It has also been reported that supported peracids can be prepared using methanesulfonic acid and hydrogen peroxide.

In this example, six heterogeneous catalysts (Car1, Suc1, Car2, Suc2, Car3, Suc3) are prepared from two different starting silicas (succinic acid and carboxylic acid) following 3 different methodologies. All these heterogeneous catalysts are colorless.

Figure 6:
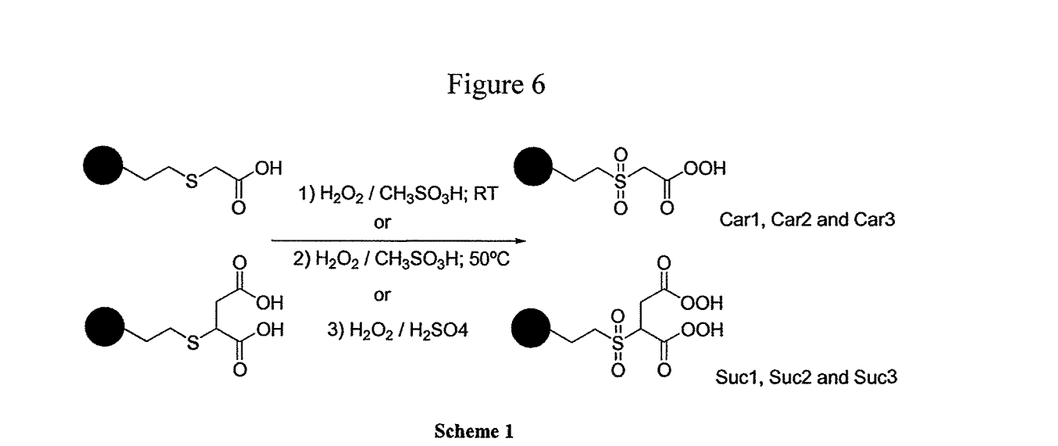
FIG. 6 is an illustration of a synthesis of a catalyst.
Figure 7:
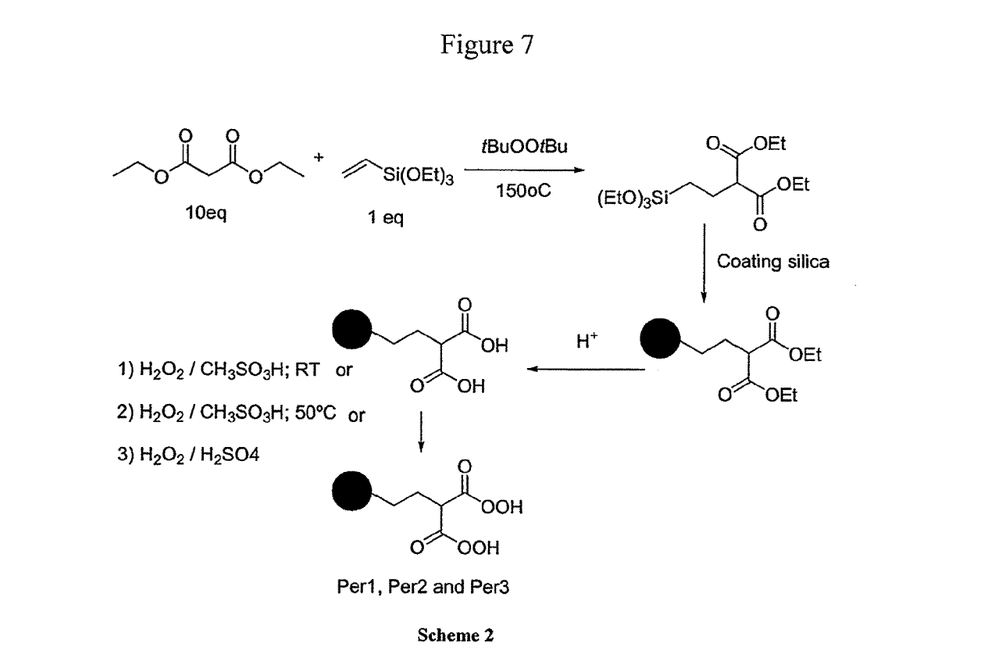
FIG. 7 is an illustration of a dicarboxylic acid without the S linkage

As shown in FIG. 6, these heterogeneous catalysts are synthesized from existing mono or dicarboxylic acids linked to the silica through sulphur functionality. An alternative heterogeneous catalyst consisting of a dicarboxylic acid without the S linkage was also synthesized (FIG. 7). Three new heterogeneous catalysts were obtained (Pen, Per2 and Per3).

Figure 8:
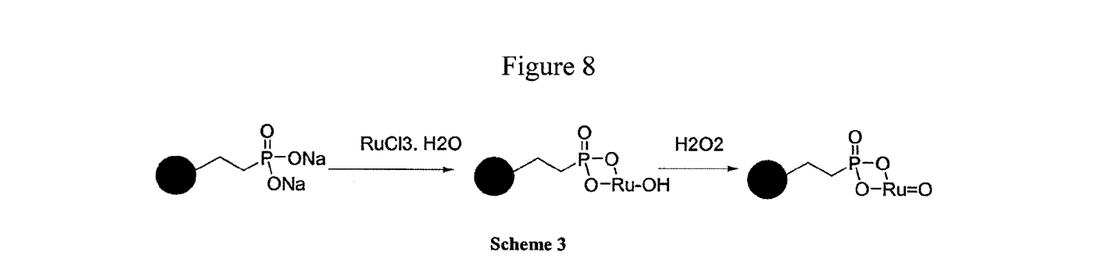
FIG. 8 is an illustration of the synthesis of oxo-ruthenium ethyl/butyl phosphonate silica (SiPORu=O).

Oxo-ruthenium catalysts are well known oxidants and so two new Ru═O heterogeneous catalysts have been prepared following two different methodologies. The, heterogeneous Ru(V) catalysts will be used to oxidize a solution of Co(II) acetate by being reduced to an heterogeneous Ru(III) catalyst. Therefore, oxo-ruthenium ethyl/butyl phosphonate silica (SiPORu═O) was synthesized as shown in FIG. 8 to give a black silica.

Figure 9:
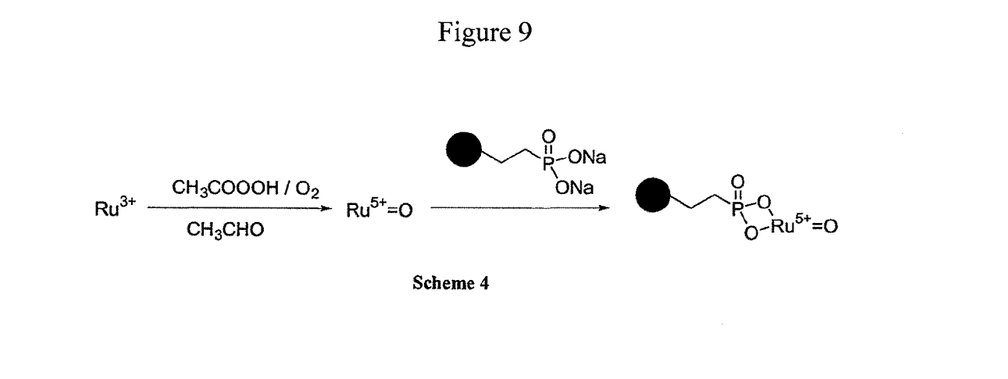
FIG. 9 is an illustration of an oxidation of Ru by using peracetic acid/acetaldehyde/0 SiPORu=O.

Alternatively, the oxidation of Ru is also reported by using peracetic acid/acetaldehyde/0 SiPORu═O was prepared as shown below following these general reaction conditions to give a dark brown silica (FIG. 9).

In both cases is assumed that it should be possible to deoxidize the heterogeneous Ru to the heterogeneous Ru.

Figure 10:
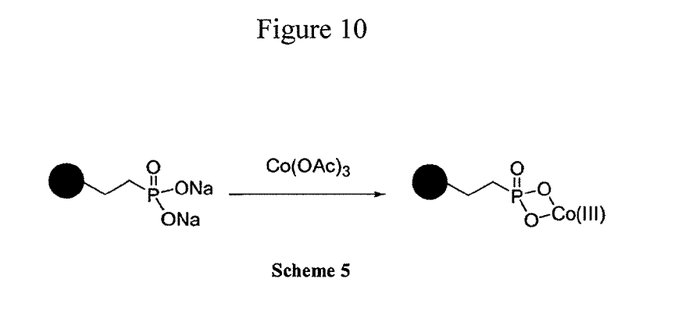
FIG. 10 is an illustration of a new Co(III) catalyst.

A new Co(III) catalyst was also prepared (FIG. 10, SiPOCo (III)). This heterogeneous catalyst might have the capability of exchanging the immobilized Co(III) with the Co(II) in solution.

Co(III) acetate was prepared by reacting Co(II) acetate with peracetic acid. The green solid was then immobilized onto the phosphonate sodium salt silica. A green silica which turned into a dark green-blue silica after drying was obtained.

Figure 11:
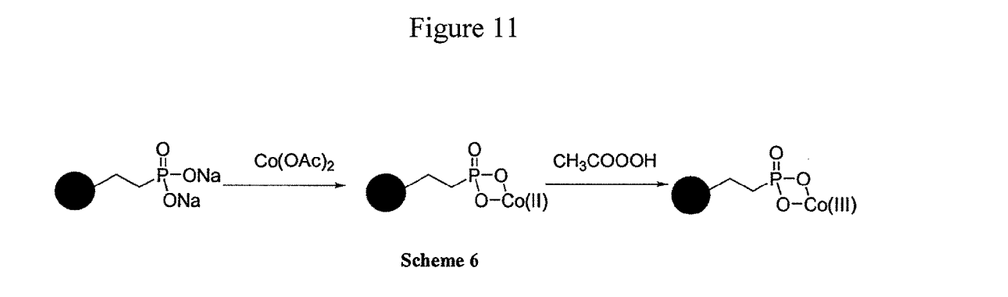
FIG. 11 is an alternate illustration of SiPOCo(III).

Alternatively, SiPOCo(III) is capable of being prepared by immobilization of Co(II) acetate onto silica to give a purple silica SiPOCo(II) which was oxidized to SiPOCo(III) upon reaction with peracetic acid (FIG. 11).

Oxidation Test Reactions

Figure 12:
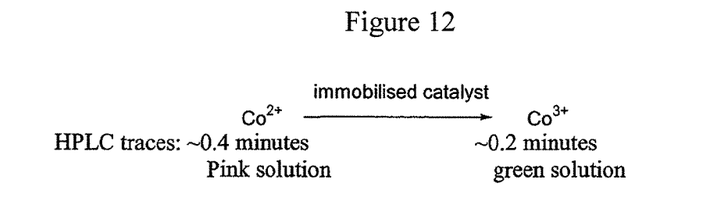
FIG. 12 is an illustration of an oxidation of a solution of cobalt (II) acetate to a solution of cobalt (III) acetate.

These new synthesized heterogeneous catalysts and two other existing heterogeneous catalysts SiPOVO and SiPOMn (both available from PhosphonicS Ltd., 114 Milton park, Abingdon, OXON, OX14 4SA, U.K.) were tested in the oxidation of a solution of cobalt (II) acetate to a solution of cobalt (III) acetate. This reaction can be followed visually (change from pink to green) as well as by HPLC, as illustrated in FIG. 12.

Oxidation test reaction conditions followed: To a solution 12 ml of Co(OAc) in water with 1% acetic acid (pink solution, 1 mL) an excess of the previously made heterogeneous catalysts (about 10 equivalents) will be added. This test reaction was first carried out at room temperature.

HPLC: Agilent Technologies 1100 Series. Phenomenex C18 column (50×4.60 mm, 3j Method: 90% H (0.1% formic acid)—10% acetonitrile (0.1% formic acid) to 10% H (0.1% formic acid)—90% acetonitrile (0.1% formic acid). Flow: 2.6 mL/min. Time: 5 minutes. Injection volume: 20 μL. UV detector at 254 nm.

1) Cobalt UH) Ethyl/Butyl Phosphonate Silica

Figure 13:
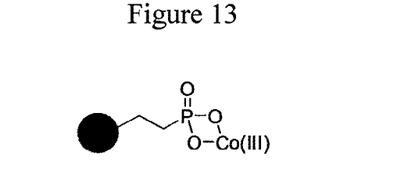
FIG. 13 is an illustration of regenerate SiPOCo(III).

Pre-formed green SiPOCO(III) converts immediately at room temperature a pink solution of Co(OAc) into a solution of about 66% of $Co^{3+}$ 34% $Co^{2+}$. The color of the solution changes to green and the silica turns brownish. This is due to the transmetallation of the Co(II) in solution with the immobilized Co(III), thus producing a mixture of immobilized Co and immobilized Co (brownish color). The method to regenerate SiPOCo(III) is via the addition of peracetic acid (as previously performed) as illustrated in FIG. 13.

Various methodologies exist to oxidize the catalyst, such as

1) Oxidation of Co(OAc) with peracetic acid to give a green solid Co(OAc) which is then immobilized using the sodium salt ethylbutyl phosphonate silica to give SiPOCo(III) as a green silica.

2) Immobilization of Co(OAc) onto the sodium salt ethylbutyl phosphonate silica (SiPOC0(II), purple silica) and oxidize this silica to SiPOCo(III), green silica.

Figure 3:
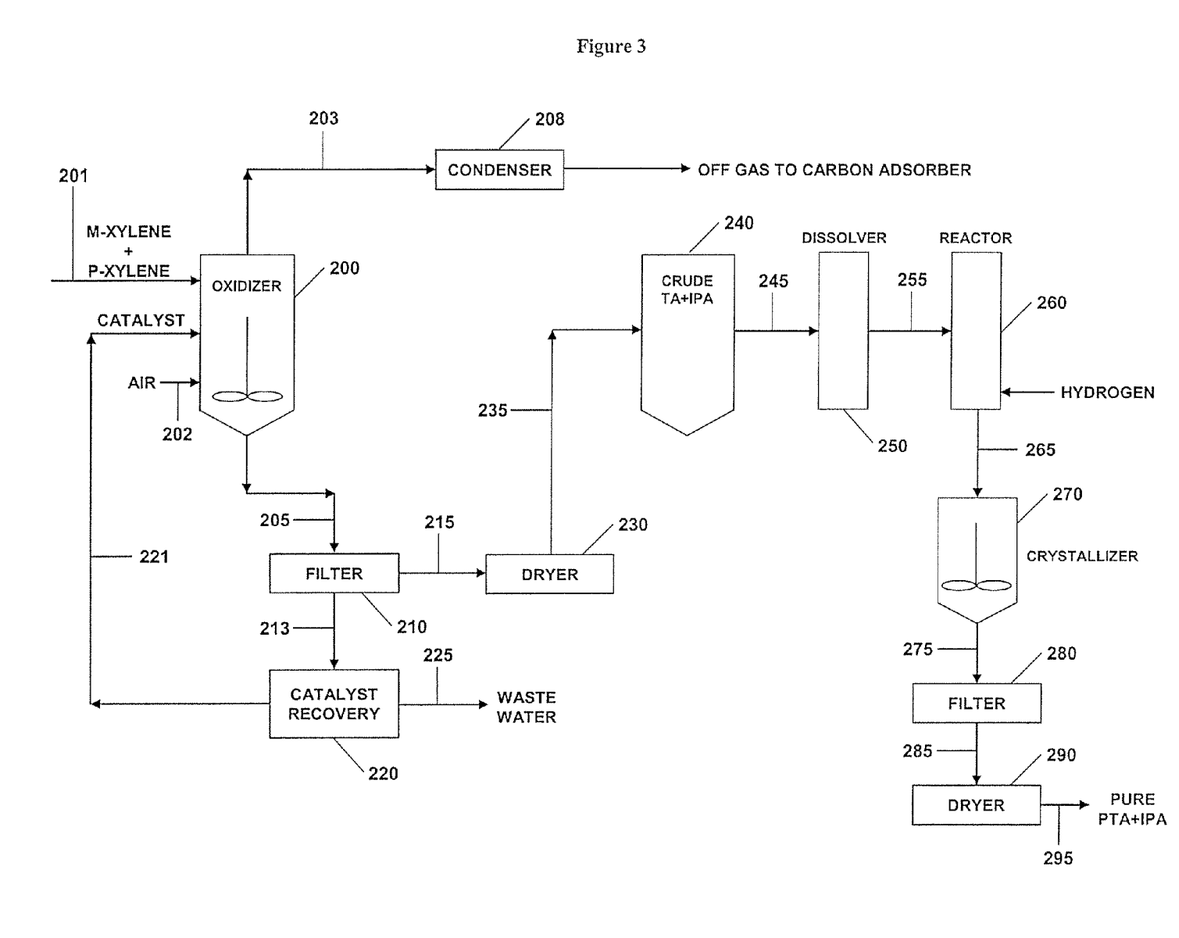
FIG. 3 is an illustration of an embodiment of a generalized flow diagram depicting a processes of preparing a supported catalyst, preparing a oxidation catalyst, and regenerating the supported catalyst.

It was decided to use the second procedure whereby a reactor can be packed with SiPOCo(II) and a solution of peracetic acid will then oxidize the fixed bed to SiPOCO(III), producing the active heterogeneous catalyst for the conversion of the solution of Co(II) acetate to Co(III) acetate (FIG. 3).

Initial studies with a mixture of hydrogen peroxide 50% and acetic acid with catalytic amount of sulfuric acid was added to the purple immobilized Co(II) catalyst and a pale green silica was obtained. The resulting heterogeneous catalyst was used to convert a solution of Co(II) to Co(III). This result was positive although optimization of each of these steps will be required in future Stages.

2) Test for the Rest of Heterogeneous Catalysts

Figure 4:
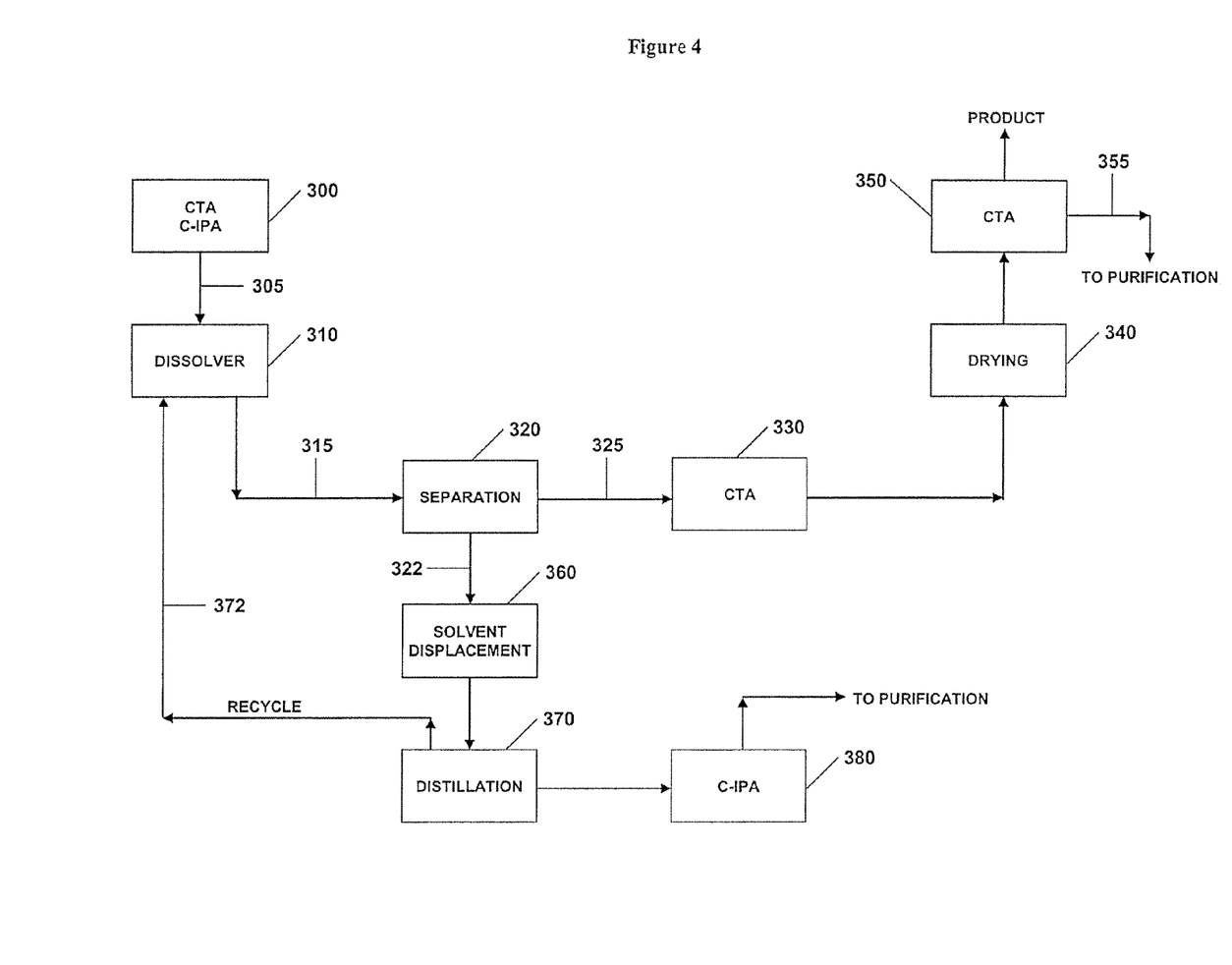
FIG. 4 is a chart illustrating various heterogeneous catalysts and the conversion of a solution of Co(II) acetate to Co(III) acetate.

The remainder of heterogeneous catalysts synthesized as previously described were also tested in the conversion of a solution of Co(II) acetate to Co(III) acetate. In all cases, immediate color changes and some bubbling were observed when adding the pink solution of Co(II) acetate to the silica. These color changes are summarized in FIG. 4. It was observed that the instant color change of the silica when adding the solution was not permanent and in some cases it changed after a few minutes.

Catalyst

The form and the particle size of the catalyst are not critical to the present invention and may vary depending, for example, on the type of reaction system employed. Non-limiting examples of the shapes of the catalyst in the present invention include balls, pebbles, spheres, extrudates, channeled monoliths, honeycombed monoliths, microspheres, pellets, or structural shapes, such as lobes, trilobes, quadralobes, pills, cakes, honeycombs, powders, granules, and the like, formed using conventional methods, such as extrusion or spray drying.

In general, the catalyst may be soluble in the reaction medium comprising solvent and the aromatic carboxylic acid precursor(s) or, alternatively, a heterogeneous catalyst may be used. The catalyst, whether homogeneous or heterogeneous, typically comprises one or more heavy metal compounds, e.g. cobalt and/or manganese compounds, and may optionally include a hydrogenation promoter. In an embodiment, the catalyst is palladium.

Where the catalyst is in heterogeneous form, it may be suitably located within the reaction zone so as to secure contact between the continuously flowing reaction medium and the catalyst. In this event, the catalyst may be suitably supported and/or constrained within the reaction zone to secure such contact without unduly constricting the flow cross-section. For instance, the heterogeneous catalyst may be coated on or otherwise applied to, or embodied in, static elements (e.g. elements forming an openwork structure) positioned of within the reaction zone so that the reaction medium flows over the same. Such static elements may additionally serve to enhance mixing of the reactants as they pass through the reaction zone. Alternatively the catalyst may be in the form of mobile pellets, particles, finely divided form, metal sponge form or the like with means being provided if necessary to confine the same to the reaction zone so that, in operation, the catalyst pellets etc become suspended or immersed in the reaction medium flowing through the reaction zone. The use of a heterogeneous catalyst in any of these ways confers the advantage of being able to confine the catalysis effect to a well-defined zone so that, once the reaction medium has traversed the zone, further hydrogenation takes place at a reduced rate or may be significantly suppressed.

A support for the hydrogenation catalyst can be less catalytically active or even inert to the hydrogenation reaction. The support may be porous and typically has a surface area, including the area of the pores on the surface, of at least 15 m$_2$/gm to 500 m$_2$/gm, e.g. from 50 m$_2$/gm to 200 m$_2$/gm, with a surface area of about 80 m$_2$/gm to about 150 m$_2$/gm being preferred. The catalyst support materials should be substantially corrosion resistant and substantially oxidation resistant under the conditions prevailing. The support component of the oxidation catalyst may be pure or a composite of materials, the latter being employed for example to impart desired chemical or physical characteristics to the catalyst. In an embodiment, the catalyst support material comprises zirconium dioxide. In an alternate embodiment, the support is carbon. In general, any catalyst will function with various embodiments of the present invention Process Now referring to FIG. 6, an embodiment of a system for performing a process of the present invention is disclosed as it is capable of use with a process for the production of an acid. In general, a feed stream 201 comprising a feed of meta-xylene and para-xylene is fed into an oxidizer 200. In this exemplary embodiment, it is contemplated that ethylbenzene plus toluene, and heavier components such as ortho-xylene have already been removed and/or minimized. Oxidizer 200 contains at least one of a solvent and a catalyst with an oxygenated gas or air being fed in as stream 202. The feed remains in oxidizer 200 for a period of time sufficient to effect oxidation of the xylenes to the respective acidic form, i.e., the para-xylene to TA and meta-xylene to IPA.

An overhead or off gas from an upper portion of oxidizer 200 is capable of being removed as stream 202 wherein the off gas can be treated such as through a condenser 208 and/or other unit such that the release of off gas, other than through an environmentally controlled manner, is reduced or eliminated.

After oxidizing, a stream 205 comprising oxidized feed stream 201, catalyst, and solvent is removed as stream 205. A separation apparatus, such as filter 210, is used to remove catalyst and/or solvent from stream 205 resulting in a stream 215. Recovered catalysts is collected in a recovery unit 220 and reprocessed in stream 221 into oxidizer 200.

Stream 215 is then dried in dryer 230 to eliminate residual moisture and/or solvent. Dried crude TA and IPA (Crude Product) is then withdrawn as stream 235 and passed into a storage tank 240.

When a purified TA and IPA is desired, Crude Product is withdrawn as stream 245 and fed to dissolver 250 which may use various solvents, heat, and/or pressure to effect dissolution of the Crude Product, as is common in the art.

The crude acid is fed as stream 255 to a hydrogenation reactor 260, where the impurities are reacted with hydrogen and the products formed are able to be separated from the acid. The resulting stream 265 is then crystallized in a series of crystallizers 270 and then fed as stream 275 to a separation device 280. A stream 285 is then dried in dryer 290 wherein a mixture of Pure Terephthalic and Isophthalic acid is withdrawn as a stream 295.

What is claimed is:

1. A process for producing an acid, said process comprising the steps of:
   a) catalytically oxidizing a liquid phase aromatic acid precursor that is selected from the group consisting of toluene, p-xylene, m-xylene, mesitylene and 2,6-dimethyl naphthalene in the presence of a gaseous oxygen source using a catalyst containing metals belonging to groups VIII, VIIB and IVB in the presence of a organic acid solvent, in an oxidation reactor;
   b) separating a finished product that is an aromatic acid;
   c) purging said solvent and reduced catalyst;
   d) recovering at least a portion of the reduced catalyst;
   e) recharging said at least a portion of the reduced catalyst over a solid recharging catalyst bed containing metals belonging to groups VIII, VIIB and IVB;

f) oxidizing the portion of the reduced catalyst by exchanging the reduced form of the metal in the reduced catalyst with the metal in the immobilized catalyst; and, g) feeding a reactivated catalyst to said oxidation reactor.

2. The process of claim 1, wherein steps (a) to g) are repeated at least one time.

3. The process of claim 1, wherein steps (a) to g) are performed in a continuous cycle.

4. The process of claim 1, further comprising the step of recycling at least a portion of said solvent into said oxidation reactor.

5. A process for converting a feed stream comprising at least meta-xylene, para-xylene, and ethylbenzene into at least one product stream comprising isophthalic acid and terephthalic acid (IPA/TA), said process comprising the steps of:
   a. removing ethylbenzene from said feed stream to produce an ethylbenzene depleted feed stream;
   b. removing ortho-xylene from said ethylbenzene depleted feed stream to produce an ortho-xylene depleted feed stream;
   c. oxidizing said ethylbenzene depleted and said ortho-xylene depleted feed stream to produce a product stream, said product stream comprising IPA/TA in a proportion between 0.5% and about 99.5% IPA and about 0.5% and about 99.5% TA using a catalyst containing metals belonging to groups VIII, VIIB and IVB;
   d. recharging said at least a portion of said catalyst over a solid recharging catalyst bed;
   e. oxidizing said portion of said catalyst by exchanging the reduced form of the metal in said catalyst with the metal in the immobilized catalyst; and
   f. adding one of either para-xylene or meta-xylene to said ethylbenzene depleted and ortho-xylene depleted feed stream.

6. The process of claim 5, wherein steps (a) to (d) are performed in a continuous cycle.

* * * * *